(12) United States Patent
Muller et al.

(10) Patent No.: US 8,712,536 B2
(45) Date of Patent: Apr. 29, 2014

(54) EYE THERAPY SYSTEM

(75) Inventors: David Muller, Boston, MA (US); Thomas Ryan, Waltham, MA (US); Ronald Scharf, Waltham, MA (US)

(73) Assignee: Avedro, Inc., Waltham, MA (US)

( * ) Notice: Subject to any disclaimer, the term of this patent is extended or adjusted under 35 U.S.C. 154(b) by 666 days.

(21) Appl. No.: 12/753,523

(22) Filed: Apr. 2, 2010

(65) Prior Publication Data
US 2010/0256705 A1    Oct. 7, 2010

Related U.S. Application Data

(60) Provisional application No. 61/166,002, filed on Apr. 2, 2009.

(51) Int. Cl.
*A61N 1/00* (2006.01)

(52) U.S. Cl.
USPC .......................................................... 607/53

(58) Field of Classification Search
USPC .......................................................... 607/53
See application file for complete search history.

(56) References Cited

U.S. PATENT DOCUMENTS

| | | |
|---|---|---|
| 3,073,310 A | 1/1963 | Mocarski |
| 3,776,230 A | 12/1973 | Neefe |
| 4,043,342 A | 8/1977 | Morrison, Jr. |
| 4,326,529 A | 4/1982 | Doss et al. |
| 4,381,007 A | 4/1983 | Doss |
| 4,429,960 A | 2/1984 | Mocilac et al. |
| 4,481,948 A | 11/1984 | Sole |
| 4,490,022 A | 12/1984 | Reynolds |
| 4,546,773 A | 10/1985 | Kremer et al. |
| 4,712,543 A | 12/1987 | Baron |
| 4,743,725 A | 5/1988 | Risman |
| 4,796,623 A | 1/1989 | Krasner et al. |

(Continued)

FOREIGN PATENT DOCUMENTS

| | | |
|---|---|---|
| EP | 1 561 440 | 8/2005 |
| EP | 1 790 383 | 5/2007 |

(Continued)

OTHER PUBLICATIONS

Chandonnet, CO2 Laser Annular Thermokeratoplasty: A Preliminary Study, Lasers in Surgery and Medicine 12:264-273 (1992), Wiley-Lill, Inc.

(Continued)

*Primary Examiner* — Michael Kahelin
*Assistant Examiner* — Alyssa M Alter
(74) *Attorney, Agent, or Firm* — Nixon Peabody LLP

(57) ABSTRACT

An electrical energy applicator in one embodiment extends from a proximal end to a distal end. The energy conducting applicator includes, at the proximal end, a connection to one or more electrical energy sources. The energy conducting applicator directs electrical energy from the one or more electrical energy sources to the distal end. The energy conducting applicator includes an outer conductor and an inner conductor extending to the distal end. The outer conductor and the inner conductor are separated by a gap. The outer conductor includes a plurality of moveable outer segments and the inner conductor includes a plurality of moveable inner segments. The plurality of outer segments and the plurality of inner segments form a total contact surface at the distal end. The total contact surface is positionable at a surface of an eye. The electrical energy is applied to the eye according to the total contact surface.

33 Claims, 8 Drawing Sheets

(56) References Cited

U.S. PATENT DOCUMENTS

| | | |
|---|---|---|
| 4,805,616 A | 2/1989 | Pao |
| 4,881,543 A | 11/1989 | Trembly et al. |
| 4,891,043 A | 1/1990 | Zeimer et al. |
| 4,943,296 A | 7/1990 | Funakubo et al. |
| 4,994,058 A | 2/1991 | Raven et al. |
| 5,019,074 A | 5/1991 | Muller |
| 5,080,660 A | 1/1992 | Buelna |
| 5,103,005 A | 4/1992 | Gyure et al. |
| 5,123,422 A * | 6/1992 | Charvin .................. 607/137 |
| 5,171,254 A | 12/1992 | Sher |
| 5,281,211 A | 1/1994 | Parel et al. |
| 5,332,802 A | 7/1994 | Kelman et al. |
| 5,368,604 A | 11/1994 | Kilmer et al. |
| 5,370,644 A | 12/1994 | Langberg |
| 5,395,385 A | 3/1995 | Kilmer et al. |
| 5,437,658 A | 8/1995 | Muller et al. |
| 5,461,212 A | 10/1995 | Seiler et al. |
| 5,490,849 A | 2/1996 | Smith |
| 5,586,134 A | 12/1996 | Das et al. |
| 5,591,185 A | 1/1997 | Kilmer et al. |
| 5,618,284 A | 4/1997 | Sand |
| 5,624,456 A | 4/1997 | Hellenkamp |
| 5,626,595 A | 5/1997 | Sklar et al. |
| 5,634,921 A | 6/1997 | Hood et al. |
| 5,658,278 A | 8/1997 | Imran et al. |
| 5,695,448 A | 12/1997 | Kimura et al. |
| 5,766,171 A | 6/1998 | Silvestrini |
| 5,779,696 A | 7/1998 | Berry et al. |
| 5,814,040 A | 9/1998 | Nelson et al. |
| 5,830,139 A | 11/1998 | Abreu |
| 5,873,901 A | 2/1999 | Wu et al. |
| 5,885,275 A | 3/1999 | Muller |
| 5,910,110 A | 6/1999 | Bastable |
| 5,919,222 A | 7/1999 | Hjelle et al. |
| 5,938,674 A | 8/1999 | Terry |
| 5,941,834 A | 8/1999 | Skladnev et al. |
| 6,033,396 A | 3/2000 | Huang et al. |
| 6,036,688 A | 3/2000 | Edwards |
| 6,053,909 A | 4/2000 | Shadduck |
| 6,101,411 A | 8/2000 | Newsome |
| 6,104,959 A | 8/2000 | Spertell |
| 6,110,182 A | 8/2000 | Mowlai-Ashtiani |
| 6,120,434 A | 9/2000 | Kimura et al. |
| 6,139,876 A | 10/2000 | Kolta |
| 6,149,646 A | 11/2000 | West, Jr. et al. |
| 6,159,194 A * | 12/2000 | Eggers et al. ................ 604/500 |
| 6,161,544 A | 12/2000 | DeVore et al. |
| 6,162,210 A | 12/2000 | Shadduck |
| 6,213,997 B1 | 4/2001 | Hood et al. |
| 6,293,938 B1 | 9/2001 | Muller |
| 6,319,273 B1 | 11/2001 | Chen et al. |
| 6,325,792 B1 | 12/2001 | Swinger et al. |
| 6,334,074 B1 | 12/2001 | Spertell |
| 6,342,053 B1 | 1/2002 | Berry |
| 6,402,739 B1 | 6/2002 | Neev |
| 6,413,255 B1 | 7/2002 | Stern |
| 6,520,956 B1 | 2/2003 | Huang |
| 6,617,963 B1 | 9/2003 | Watters et al. |
| 6,749,604 B1 | 6/2004 | Eggers et al. |
| 6,918,906 B2 | 7/2005 | Long |
| 6,946,440 B1 | 9/2005 | DeWoolfson |
| 7,044,945 B2 | 5/2006 | Sand |
| 7,130,835 B2 | 10/2006 | Cox et al. |
| 7,141,049 B2 | 11/2006 | Stern et al. |
| 7,192,429 B2 | 3/2007 | Trembly |
| 7,270,658 B2 | 9/2007 | Woloszko et al. |
| 7,402,562 B2 | 7/2008 | DeWoolfson |
| 7,651,506 B2 | 1/2010 | Bova et al. |
| 7,713,268 B2 | 5/2010 | Trembly |
| 7,875,024 B2 | 1/2011 | Turovskiy et al. |
| 7,976,542 B1 | 7/2011 | Cosman et al. |
| 8,177,778 B2 | 5/2012 | Muller et al. |
| 8,202,272 B2 | 6/2012 | Muller et al. |
| 8,348,935 B2 | 1/2013 | Muller et al. |
| 8,398,628 B2 | 3/2013 | Muller |
| 8,409,189 B2 | 4/2013 | Muller |
| 2001/0021844 A1 | 9/2001 | Kurtz et al. |
| 2001/0034502 A1 | 10/2001 | Moberg et al. |
| 2001/0039422 A1 | 11/2001 | Carol et al. |
| 2002/0002369 A1 | 1/2002 | Hood |
| 2002/0013579 A1 | 1/2002 | Silvestrini |
| 2002/0022873 A1* | 2/2002 | Erickson et al. ............... 607/117 |
| 2002/0035345 A1 | 3/2002 | Beck |
| 2002/0049437 A1 | 4/2002 | Silvestrini |
| 2002/0077699 A1 | 6/2002 | Olivieri et al. |
| 2002/0091323 A1 | 7/2002 | Dreher |
| 2002/0091401 A1 | 7/2002 | Hellenkamp |
| 2002/0099363 A1 | 7/2002 | Woodward et al. |
| 2002/0143326 A1 | 10/2002 | Foley et al. |
| 2002/0164379 A1 | 11/2002 | Nishihara et al. |
| 2003/0018255 A1 | 1/2003 | Martin et al. |
| 2003/0097130 A1 | 5/2003 | Muller et al. |
| 2003/0167061 A1 | 9/2003 | Schlegel et al. |
| 2003/0175259 A1 | 9/2003 | Karageozian |
| 2003/0181903 A1 | 9/2003 | Hood et al. |
| 2003/0216728 A1 | 11/2003 | Stern et al. |
| 2004/0001821 A1 | 1/2004 | Silver et al. |
| 2004/0002640 A1 | 1/2004 | Luce |
| 2004/0049186 A1 | 3/2004 | Hood et al. |
| 2004/0111086 A1 | 6/2004 | Trembly |
| 2004/0143250 A1 | 7/2004 | Trembly |
| 2004/0199158 A1 | 10/2004 | Hood et al. |
| 2004/0243160 A1 | 12/2004 | Shiuey et al. |
| 2005/0033202 A1 | 2/2005 | Chow et al. |
| 2005/0070977 A1 | 3/2005 | Molina |
| 2005/0131401 A1 | 6/2005 | Malecki et al. |
| 2005/0183732 A1 | 8/2005 | Edwards |
| 2005/0197657 A1 | 9/2005 | Goth et al. |
| 2005/0241653 A1 | 11/2005 | Van Heugten et al. |
| 2005/0267332 A1 | 12/2005 | Paul et al. |
| 2005/0287217 A1 | 12/2005 | Levin et al. |
| 2006/0135957 A1 | 6/2006 | Panescu |
| 2006/0149343 A1 | 7/2006 | Altshuler et al. |
| 2006/0189964 A1 | 8/2006 | Anderson et al. |
| 2006/0206110 A1 | 9/2006 | Knowlton et al. |
| 2006/0254851 A1 | 11/2006 | Karamuk |
| 2006/0287649 A1 | 12/2006 | Ormsby et al. |
| 2006/0287662 A1 | 12/2006 | Berry et al. |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0074730 A1 | 4/2007 | Nanduri et al. |
| 2007/0114946 A1 | 5/2007 | Goetze et al. |
| 2007/0123845 A1 | 5/2007 | Lubatschowski |
| 2007/0161976 A1 | 7/2007 | Trembly |
| 2007/0179564 A1 | 8/2007 | Harold |
| 2007/0191909 A1* | 8/2007 | Ameri et al. .................... 607/54 |
| 2007/0203547 A1 | 8/2007 | Costello et al. |
| 2007/0244470 A1 | 10/2007 | Barker et al. |
| 2007/0244496 A1 | 10/2007 | Hellenkamp |
| 2008/0015660 A1 | 1/2008 | Herekar |
| 2008/0027328 A1 | 1/2008 | Klopotek et al. |
| 2008/0300590 A1 | 12/2008 | Horne et al. |
| 2009/0024117 A1* | 1/2009 | Muller ........................... 606/20 |
| 2009/0054879 A1 | 2/2009 | Berry |
| 2009/0069798 A1 | 3/2009 | Muller et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0187173 A1 | 7/2009 | Muller |
| 2009/0187178 A1 | 7/2009 | Muller et al. |
| 2009/0209954 A1 | 8/2009 | Muller et al. |
| 2009/0275936 A1 | 11/2009 | Muller |
| 2010/0094197 A1 | 4/2010 | Marshall et al. |
| 2010/0094280 A1 | 4/2010 | Muller |
| 2010/0179531 A1 | 7/2010 | Nebrigic et al. |
| 2010/0185192 A1 | 7/2010 | Muller et al. |
| 2010/0256626 A1 | 10/2010 | Muller et al. |
| 2010/0280509 A1 | 11/2010 | Muller et al. |
| 2013/0131664 A1 | 5/2013 | Muller et al. |

(56) References Cited

U.S. PATENT DOCUMENTS

FOREIGN PATENT DOCUMENTS

| EP | 2 269 531 | 1/2011 |
|---|---|---|
| FR | 2 818 119 | 6/2002 |
| WO | WO 99/017690 | 4/1999 |
| WO | WO 00/009027 | 2/2000 |
| WO | 0074648 A2 | 12/2000 |
| WO | WO 03/002008 | 1/2003 |
| WO | WO 2004/052223 | 6/2004 |
| WO | 2006128038 A2 | 11/2006 |
| WO | WO 2007/022993 | 3/2007 |
| WO | 2007/120457 A2 | 10/2007 |
| WO | WO 2008/008330 | 1/2008 |
| WO | WO 2009/012490 | 1/2009 |
| WO | WO 2009/073213 | 6/2009 |
| WO | WO 2009/094467 | 7/2009 |
| WO | WO 2010/039854 | 4/2010 |
| WO | WO 2011/050164 | 4/2011 |

OTHER PUBLICATIONS

Muller et al., Br. J. Opthalmol 2001; 85:437-443 (Apr.).
Naoumidi et al., J. Cataract Refract Surg. May 2006; 32(5):732-41.
Pallikaris et al., J. Cataract Refract Surg. Aug. 2005; 31(8):1520-29.
Acosta et al., Cornea. Aug. 2006;25(7):830-8.
Alió JL, Amparo F, Ortiz D, Moreno L, "Corneal Multifocality With Excimer Laser for Presbyopia Correction," *Current Opinion in Ophthalmology*, vol. 20, Jul. 2009, pp. 264-271 (8 pages).
Alió JL, Chaubard JJ, Caliz A, Sala E, Patel S, "Correction of Presbyopia by Technovision Central Multifocal LASIK (PresbyLASIK)," *Journal of Refractive Surgery*, vol. 22, May 2006, pp. 453-460 (8 pages).
Anderson K, El-Sheikh A, Newson T, "Application of Structural Analysis to the Mechanical Behavior of the Cornea," *Journal of the Royal Society Interface*, vol. 1, May 2004, pp. 3-15 (13 pages).
Andreassen TT, Simonsen AH, Oxlund H, "Biomechanical Properties of Keratoconus and Normal Corneas," *Experimental Eye Research*, vol. 31, Oct. 1980, pp. 435-441 (7 pages).
Anschutz T, "Laser Correction of Hyperopia and Presbyopia," *International Ophthalmology Clinics*, vol. 34, No. 4, Fall 1994, pp. 107-137 (33 pages).
Bailey MD, Zadnik K, "Outcomes of LASIK for Myopia With FDA-Approved Lasers," *Cornea*, vol. 26, No. 3, Apr. 2007, pp. 246-254 (9 pages).
Borja D, Manns F, Lamar P, Rosen A, Fernandez V, Parel JM, "Preparation and Hydration Control of Corneal Tissue Strips for Experimental Use," *Cornea*, vol. 23, No. 1, Jan. 2004, pp. 61-66 (7 pages).
Bower KS, Weichel ED, Kim TJ, "Overview of Refractive Surgery," *Am Fam Physician*, vol. 64, No. 7, Oct. 2001, pp. 1183-1190 (8 pages).
Braun EH, Lee J, Steinert RF, "Monovision in LASIK," *Ophthalmology*, vol. 115, No. 7, Jul. 2008, pp. 1196-1202 (7 pages).
Bryant MR, Marchi V, Juhasz T, "Mathematical Models of Picosecond Laser Keratomileusis for High Myopia," *Journal of Refractive Surgery*, vol. 16, No. 2, Mar.-Apr. 2000, pp. 155-162 (9 pages).
Bryant MR, McDonnell PJ, "Constitutive Laws for Biomechanical Modeling of Refractive Surgery," *Journal of Biomechanical Engineering*, vol. 118, Nov. 1996, pp. 473-481 (10 pages).
Buzard KA, Fundingsland BR, "Excimer Laser Assisted in Situ Keratomileusis for Hyperopia," *Journal of Cataract & Refractive Surgery*, vol. 25, Feb. 1999, pp. 197-204 (8 pages).
Charman WN, "The Eye in Focus: Accommodation and Presbyopia," *Clinical and Experimental Optometry*, vol. 91, May 2008, pp. 207-225 (19 pages).
Corbett et al, "Effect of Collagenase Inhibitors on Coreal Haze after PRK", Exp. Eye Res., vol. 72, Issue 3, pp. 253-259, dated Jan. 29, 2001 (7 pages).
Cox CA, Krueger RR, "Monovision with Laser Vision Correction," *Ophthalmology Clinics of North Amermica*, vol. 19, No. 1, Mar. 2006, pp. 71-75 (7 pages).

Doss JD, Albillar JI, "A Technique for the Selective Heating of Corneal Stroma," *Contact & Intraocular Lens Medical Journal*, vol. 6, No. 1, Jan.-Mar. 1980, pp. 13-17 (8 pages).
Elsheikh A, Anderson K, "Comparative Study of Corneal Strip Extensometry and Inflation Tests," *Journal of the Royal Society Interface*, vol. 2, May 2005, pp. 177-185 (10 pages).
Evans BJW, "Monovision: a Review," *Ophthalmic and Physiological Optics*, vol. 27, Jan. 2007, pp. 417-439 (23 pages).
Gasset AR, Kaufman HE, "Thermokeratoplasty in the Treatment of Keratoconus," *American Journal of Ophthalmology*, vol. 79, Feb. 1975, pp. 226-232 (8 pages).
Gloster J, Perkins ES, "The Validity of the Imbert-Flick Law as Applied to Applanation Tonometry," *Experimental Eye Research*, vol. 2, Jul. 1963, pp. 274-283 (10 pages).
Gupta N, Naroo SA, "Factors Influencing Patient Choice of Refractive Surgery or Contact Lenses and Choice of Centre," *Contact Lens & Anterior Eye*, vol. 29, Mar. 2006, pp. 17-23 (7 pages).
Hamilton DR, Hardten DR, Lindstrom RL, "Thermal Keratoplasty," *Cornea*, $2^{nd}$ Edition, Chapter 167, 2005, pp. 2033-2045 (13 pages).
Hersh PS, "Optics of Conductive Keratoplasty: Implication for Presbyopia Management," *Transactions of the American Ophthalmological Society*, vol. 103, 2005, pp. 412-456 (45 pages).
Hjortdal JO, "Extensibility of the Normo-Hydrated Human Cornea," *Acta Ophthalmologica Scandinavica*, vol. 73, No. 1, Feb. 1995, pp. 12-17 (7 pages).
Hori-Komai Y, Toda I, Asano-Kato N, Tsubota K, "Reasons for Not Performing Refractive Surgery," *Journal of Cataract & Refractive Surgery*, vol. 28, May 2002, pp. 795-797 (3 pages).
Illueca C, Alió Jl, Mas D, Ortiz D, Perez J, Espinosa J, Esperanza S, "Pseudoaccommodation and Visual Acuity with Technovision PresbyLASIK and a Theoretical Simulated Array® Multifocal Intraocular Lens," *Journal of Refractive Surgery*, vol. 24, Apr. 2008, pp. 344-349 (6 pages).
Jain S, Arora I, Azar DT, "Success of Monovision in Presbyopes: Review of the Literature and Potential Applications to Refractive Surgery," *Survey of Ophthalmology*, vol. 40, No. 6, May-Jun. 1996, pp. 491-499 (9 pages).
Tin GJC, Lyle A, Merkley KH, "Laser in Situ Keratomileusis for Primary Hyperopia," *Journal of Cataract & Refractive Surgery*, vol. 31, Apr. 2005, pp. 776-784 (9 pages).
Kaliske M, "A Formulation of Elasticity and Viscoelasticity for Fibre Reinforced Material at Small and Finite Strains," *Computer Methods in Applied Mechanics and Engineering*, vol. 185, 2000, pp. 225-243 (19 pages).
Llovet F, Galal A, Benitez-del-Castillo J-M, Ortega J, Martin C, Baviera J, "One-Year Results of Excimer Laser in Situ Keratomileusis for Hyperopia," *Journal of Cataract & Refractive Surgery*, vol. 35, Jul. 2009, pp. 1156-1165 (10 pages).
Louie TM, Applegate D, Kuenne CB, Choi LJ, Horowitz DP, "Use of Market Segmentation to Identify Untapped Consumer Needs in Vision Correction Surgery for Future Growth," *Journal of Refractive Surgery*, vol. 19, No. 5, Sep.-Oct. 2003, pp. 566-576 (12 pages).
Maxwell WA, Lane SS, Zhou F, "Performance of Presbyopia-Correcting Intraocular Lenses in Distance Optical Bench Tests," *Journal of Cataract & Refractive Surgery*, vol. 35, Jan. 2009, pp. 166-171 (6 pages).
McDonald MB, Durrie D, Asbell P, Maloney R, Nichamin L, "Treatment of Presbyopia With Conductive Keratoplasty: Six-Month Results of the 1-Year United States FDA Clinical Trial," *Cornea*, vol. 23, No. 7, Oct. 2004, pp. 661-668 (8 pages).
McDonald MB, "Conductive Keratoplasty: a Radiofrequency-Based Technique for the Correction of Hyperopia," *Transactions of the American Ophthalmological Society*, vol. 103, Dec. 2005, pp. 512-536 (25 pages).
Moriera MD, Garbus JJ, Fasano A, Lee M, Clapham TN, McDonnel PJ, "Multifocal Corneal Topographic Changes With Excimer Laser Photorefractive Keratectomy," *Archives of Ophthalmology*, vol. 110, Jul. 1992, pp. 994-999 (6 pages).
Nash IS, Greene PR, Foster CS, "Comparison of Mechanical Properties of Keratoconus and Normal Corneas," *Experimental Eye Research*, vol. 35, 1982, pp. 413-424 (12 pages).

(56) References Cited

OTHER PUBLICATIONS

Newman JM, "Analysis, Interpretation, and Prescription for the Ametropias and Heterophorias," *Borish's Clinical Refraction*, 1998, pp. 776-822 (49 pages).
Pandolfi A, Manganiello F, "A Model for the Human Cornea: Formulation and Numerical Analysis," *Biomechanics and Modeling in Mechanobiology*, vol. 5, Jan. 2006, pp. 237-246 (10 pages).
Pertaub R, Ryan TP, "Numerical Model and Analysis of an Energy-Based System Using Microwaves for Vision Correction," *Proceedings of SPIE*, vol. 7181, Feb. 2009, p. 718105-1 to 718105-14 (14 pages).
Petroll WM, Roy P, Chuong CJ, Hall B, Cavanagh HD, Jester JV, "Measurement of Surgically Induced Corneal Deformations Using Three-Dimensional Confocal Microscopy," *Cornea*, vol. 15, No. 2, Mar. 1996, pp. 154-164 (12 pages).
Pinelli R, Ortiz D, Simonetto A, Bacchi C, Sala E, Alió JL, "Correction of Presbyopia in Hyperopia With a Center-Distance Paracentral-Near Technique Using the Technolas 217Z Platform," *Journal of Refractive Surgery*, vol. 24, May 2008, pp. 494-500 (7 pages).
Pinsky PM, Datye DV, "A Microstructurally-Based Finite Element Model of the Incised Human Cornea," *Journal of Biomechanics*, vol. 24, No. 10, Apr. 1991, pp. 907-922 (15 pages).
Pinsky PM, Datye DV, "Numerical Modeling of Radial, Astigmatic, and Hexagonal Keratotomy," *Refractive and Corneal Surgery*, vol. 8, No. 2, Mar.-Apr. 1992, pp. 164-172 (11 pages).
Pinsky PM, van der Heide D, Chernyak D, "Computational Modeling of Mechanical Anisotropy in the Cornea and Sclera," *Journal of Cataract & Refractive Surgery*, vol. 31, Jan. 2005, pp. 136-145 (10 pages).
Riley C, Chalmers RL, "Survey of Contact Lens-Wearing Habits and Attitudes Toward Methods of Refractive Correction: 2002 Versus 2004," *Optometry and Vision Science*, vol. 82, No. 6, Jun. 2005, pp. 555-561 (7 pages).
Rosenbloom A, "New Aged and Old Aged: Impact of the Baby Boomer," *Journal of the American Optometry Association*, vol. 74, No. 4, Apr. 2003, pp. 211-213 (5 pages).
Rutzen AR, Roberts CW, Driller J, Gomez D, Lucas BC, Lizzi FL, Coleman DJ., "Production of Corneal Lesions Using High-Intensity Focused Ultrasound," *Cornea*, vol. 9, No. 4, Oct. 1990, pp. 324-330 (8 pages).
Ryan TP, Pertaub R, Meyers SR, Dresher RP, Scharf R., "Experimental Results of a New System Using Microwaves for Vision Correction," *Proceedings of SPIE*, vol. 7181, Feb. 2009, pp. 718106.1 to 718106.17 (17 pages).
Seiler T, Matallana M, Bende T, "Laser Thermokeratoplasty by Means of a Pulsed Holmium: YAG Laser for Hyperopic Correction," *Refractive and Corneal Surgery*, vol. 6, No. 5, Sep.-Oct. 1990, pp. 335-339 (6 pages).
Seiler T, Matallana M, Sendler S, Bende T, "Does Bowman's Layer Determine the Biomechanical Properties of the Cornea?" *Refractive and Corneal Surgery*, vol. 8, No. 2, Mar.-Apr. 1992, pp. 139-142 (6 pages).
Shin TJ, Vito RP, Johnson LW, McCarey BE, "The Distribution of Strain in the Human Cornea," *Journal of Biomechanics*, vol. 30, No. 5, May 1997, pp. 497-503 (7 pages).
Solomon KD, Fernandez de Castro LE, Sandoval HP, Biber JM, Groat B, Neff KD, Ying MS, French JW, Donnenfeld ED, Lindstrom RL, "LASIK World Literature Review: Quality of Life and Patient Satisfaction," *Ophthalmology*, vol. 116, No. 4, Apr. 2009, pp. 691-701 (11 pages).
Stanley PF, Tanzer DJ, Schallhorn SC, "Laser Refractive Surgery in the United States Navy," *Current Opinion Ophthalmology*, vol. 19, Jul. 2008, pp. 321-324 (4 pages).
Strenk SA, Strenk LM, Koretz JF, "The Mechanism of Presbyopia," *Progress in Retinal Eye Research*, vol. 24, May 2005, pp. 379-393 (15 pages).
Stringer H, Parr J., "Shrinkage Temperature of Eye Collagen," *Nature*, Dec. 1964, p. 1307 (1 page).
Sutton G., Patmore A.L., Joussen A.M., Marshall J., "Mannose 6-Phosphate Reduces Haze Following Excimer Laser Photorefractive Keratectomry," *Lasers and Light*, vol. 7, No. 2/3, 1996, pp. 117-119 (3 pages).
Telandro A., "Pseudo-Accommodation Cornea: a New Concept for Correction of Presbyopia," *Journal of Refractive Surgery*, vol. 20, No. 5, Sep.-Oct. 2004, pp. S714-S717 (5 pages).
Trembly BS, Hashizume N, Moodie KL, Cohen KL, Tripoli NK, Hoopes PJ, "Microwave Thermal Keratoplasty for Myopia: Keratoscopic Evaluation in Porcine Eyes," *Journal of Refractive Surgery*, vol. 17, No. 6, Nov.-Dec. 2001, pp. 682-688 (8 pages).
Trembly BS, Keates RH, "Combined Microwave Heating and Surface Cooling of the Cornea," *IEEE Transactions on Biomedical Engineering*, vol. 38, No. 1, Jan. 1991, pp. 85-91 (8 pages).
Truscott RJ, "Presbyopia Emerging from a Blur Towards an Understanding of the Molecular Basis for this Most Common Eye Condition," *Experimental Eye Research*, vol. 88, Feb. 2009, pp. 241-247 (7 pages).
Uchio E, Ohno S, Kudoh J, Aoki K, Kisielewicz LT, "Simulation Model of an Eyeball Based on Finite Element Analysis on a Supercomputer," *British Journal of Ophthalmology*, vol. 83, Jun. 1999, pp. 1106-0011 (7 pages).
Wang JQ, Zeng YJ, Li XY, "Influence of Some Operational Variables on the Radial Keratotomy Operation," *British Journal of Ophthalmology*, vol. 84, Jan. 2000, pp. 651-6533 (4 pages).
Wollensak, G., et al., "Riboflavin/Ultraviolet-A-Induced Collagen Crosslinking for the Treatment of Keratoconus," *American Journal of Ophthalmology, Ophthalmic Publ.*, Chicago, IL, US, vol. 135, No. 5, May 1, 2003, pp. 620-627 (8 pages).
Zelichowska B, Rekas M, Stankiewicz A, Cervino A, Montés-Micó R., "Apodized Diffractive Versus Refractive Multifocal Intraocular Lenses: Optical and Visual Evaluation," *Journal of Cataract & Refractive Surgery*, vol. 34, Dec. 2008, pp. 2036-2042 (7 pages).
International Search Report for PCT/US2010/029806 dated Jun. 1, 2010 (3 pages).
Written Opinion for PCT/US2010/029806 dated Jun. 1, 2010 (6 pages).
International Search Report for PCT/US2010/029791 dated Jun. 1, 2010 (3 pages).
Written Opinion for PCT/US2010/029791 dated Jun. 1, 2010 (6 pages).
Trembly et al.; Microwave Thermal Keratoplasty for Myopia: Keratoscopic Evaluation in Procine Eyes; Journal of Refractive Surgery; vol. 17; Nov./Dec. 2001; (8 pages).
Morlet N., Minassian D., Dart J., "Astigmatism and the analysis of its surgical correction", Br f Ophthalmol 2001; 85: pp. 1127-1138.
Berjano et al.; "Radio-Frequency Heating of the Cornea: Theoretical Model and In Vitro Experiments"; IEEE Transactions on Biomedical Engineering; vol. 49; No. 3; Mar. 2002; pp. 196-205.
Berjano et. al.; "Ring Electrode for Radio-Frequency Heating of the Cornea: Modelling and In Vitro Experiments"; Medical & Biological Engineering & Computing 2003; vol. 41; pp. 630-639.
International Search Report mailed Aug. 14, 2009 for PCT/US2009/042204, (5 pages).
International Search Report mailed Nov. 20, 2009 for PCT/2009/059061 (3 pages).
International Search Report mailed Nov. 6, 2009 for PCT/US2009/057481 (2 pages).

\* cited by examiner

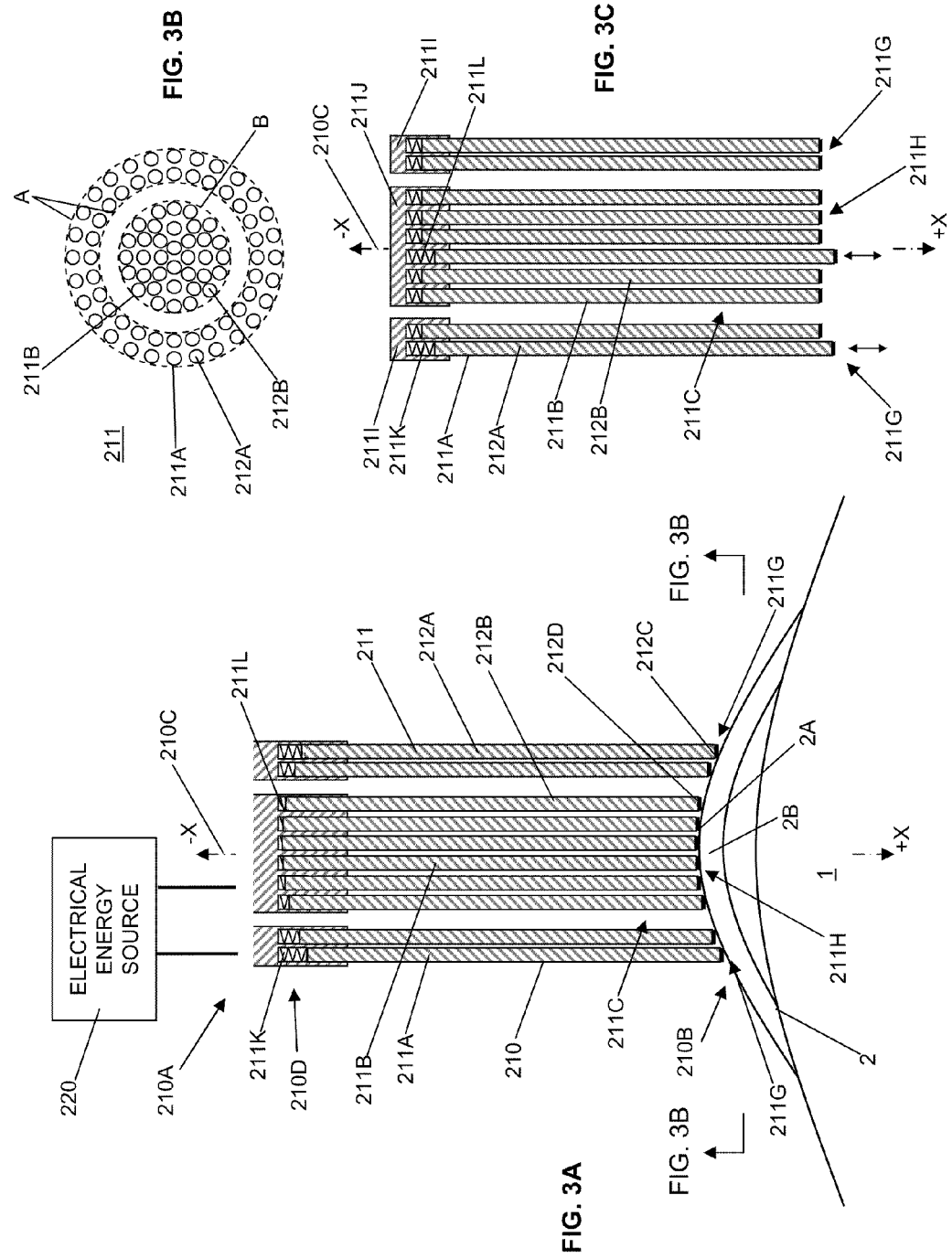

EYE THERAPY SYSTEM

CROSS-REFERENCE TO RELATED APPLICATIONS

This application claims the benefit of priority from U.S. Provisional Application No. 61/166,002, filed Apr. 2, 2009, which is hereby incorporated by reference in its entirety.

BACKGROUND OF THE INVENTION

1. Field of the Invention

The invention pertains to the field of keratoplasty and, more particularly, to a system configured to achieve adjustable contact with an eye to apply thermokeratoplasty.

2. Description of Related Art

A variety of eye disorders, such as myopia, keratoconus, and hyperopia, involve abnormal shaping of the cornea. Keratoplasty reshapes the cornea to correct such disorders. For example, with myopia, the shape of the cornea causes the refractive power of an eye to be too great and images to be focused in front of the retina. Flattening aspects of the cornea's shape through keratoplasty decreases the refractive power of an eye with myopia and causes the image to be properly focused at the retina.

Invasive surgical procedures, such as laser-assisted in-situ keratomileusis (LASIK), may be employed to reshape the cornea. However, such surgical procedures typically require a healing period after surgery. Furthermore, such surgical procedures may involve complications, such as dry eye syndrome caused by the severing of corneal nerves.

Thermokeratoplasty, on the other hand, is a noninvasive procedure that may be used to correct the vision of persons who have disorders associated with abnormal shaping of the cornea, such as myopia, keratoconus, and hyperopia. Thermokeratoplasty may be performed by applying electrical energy, for example, in the microwave band or radio frequency (RF) band. In particular, microwave thermokeratoplasty may employ a near field microwave applicator to apply energy to the cornea and raise the corneal temperature. At about 60° C., the collagen fibers in the cornea shrink. The onset of shrinkage is rapid, and stresses resulting from this shrinkage reshape the corneal surface. Thus, application of heat energy according to particular patterns, including, but not limited to, circular or annular patterns, may cause aspects of the cornea to flatten and improve vision in the eye.

SUMMARY

In general, the pattern of energy applied to a cornea during thermokeratoplasty depends on how the energy applicator is applied against the cornea. Embodiments according to aspects of the present invention account for the shape of the cornea when the applicator is positioned to deliver energy and can be selectively configured to apply energy to the cornea according to a selected pattern and/or penetration depth.

An electrical energy applicator in one embodiment extends from a proximal end to a distal end. The energy conducting applicator includes, at the proximal end, a connection to one or more electrical energy sources. The energy conducting applicator directs electrical energy from the one or more electrical energy sources to the distal end. The distal end is positionable at a surface of an eye. The energy conducting applicator includes an outer conductor and an inner conductor extending to the distal end. The outer conductor and the inner conductor are separated by a gap. The outer conductor includes a plurality of moveable outer segments and the inner conductor includes a plurality of moveable inner segments. The plurality of outer segments and the plurality of inner segments form a total contact surface at the distal end. The total contact surface is positionable at a surface of an eye. The electrical energy is applied to the eye according to the total contact surface.

In operation, the total contact surface area of the electrical energy applicator is positioned at a surface of an eye, and electrical energy is applied through the electrical energy conducting applicator to the eye according to the total contact surface.

These and other aspects of the present invention will become more apparent from the following detailed description of the preferred embodiments of the present invention when viewed in conjunction with the accompanying drawings.

BRIEF DESCRIPTION OF THE DRAWINGS

FIG. 3A illustrates a view of a system that achieves adjustable contact between the energy conducting element and the eye according to aspects of the present invention.

FIG. 3B illustrates a view of the energy conducting element of the system of FIG. 3A.

FIG. 3C illustrates another view of the energy conducting element of the system of FIG. 3A.

DESCRIPTION

In general, the pattern of energy applied to a cornea during thermokeratoplasty depends on how the energy applicator is applied against the cornea. To apply the desired pattern of energy to the cornea, aspects of the present invention account for the shape of the cornea when the applicator is positioned to deliver energy. In particular, an energy conducting element of the applicator includes a plurality of movable segments that can adjust to the shape of the cornea. The plurality of movable segments therefore defines a total contact surface that corresponds to the shape of the cornea and provides the desired contact for the delivery of energy. The plurality of movable segments can also be selectively configured to apply energy to the cornea according to a selected pattern and/or penetration depth.

Figure 1:
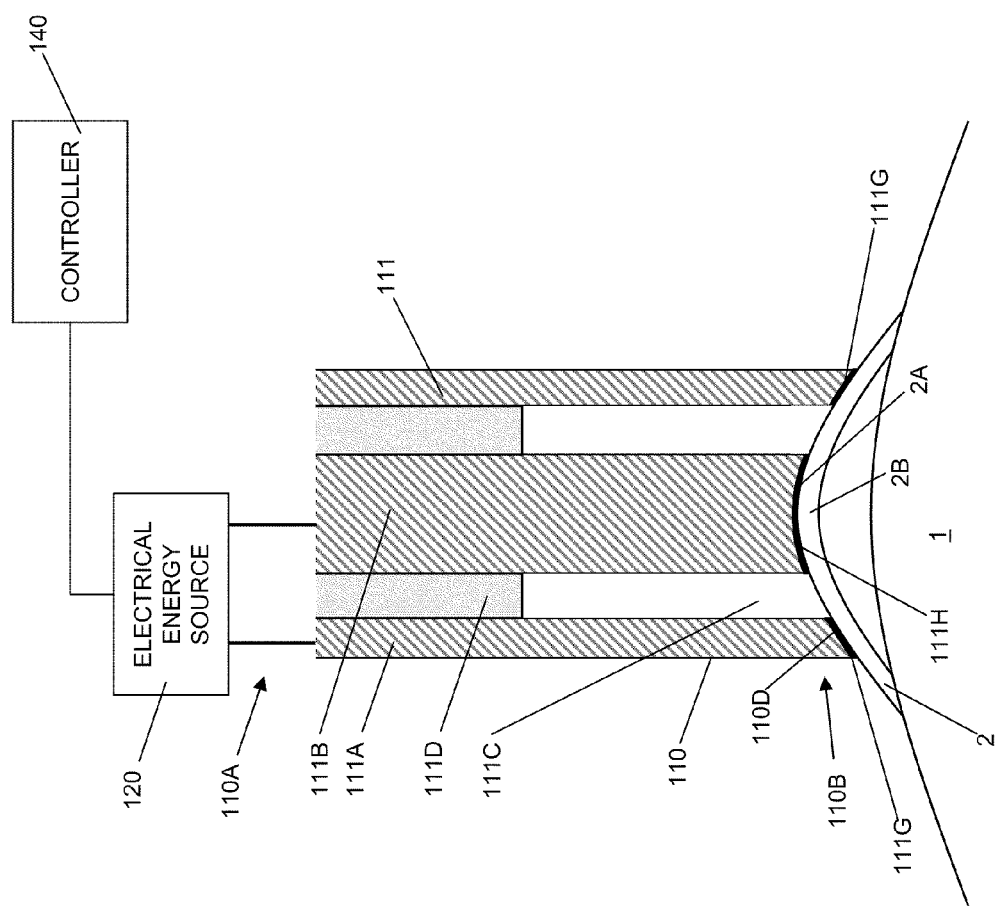
FIG. 1 illustrates a system for applying heat to a cornea of an eye to cause reshaping of the cornea.

FIG. 1 illustrates an example system for applying energy to a cornea 2 of an eye 1 to generate heat and cause reshaping of the cornea. In particular, FIG. 1 shows an applicator 110 with an electrical energy conducting element 111 that is operably connected to an electrical energy source 120, for example, via conventional conducting cables. The electrical energy conducting element 111 extends from a proximal end 110A to a distal end 110B of the applicator 110. The electrical energy conducting element 111 conducts electrical energy from the source 120 to the distal end 110B to apply heat energy to the cornea 2, which is positioned at the distal end 110B. In particular, the electrical energy source 120 may include a microwave oscillator for generating microwave energy. For example, the oscillator may operate at a microwave frequency range of about 400 MHz to about 3000 MHz, and more specifically at a frequency of around 915 MHz or around 2450 MHz, which has been safely used in other applications. As used herein, the term "microwave" may generally correspond to a frequency range from about 10 MHz to about 10 GHz.

As further illustrated in FIG. 1, the electrical energy conducting element 111 may include two microwave conductors 111A and 111B, which extend from the proximal end 110A to the distal end 110B of the applicator 110. In particular, the conductor 111A may be a substantially cylindrical outer conductor, while the conductor 111B may be a substantially cylindrical inner conductor that extends through an inner passage extending through the conductor 111A. With the inner passage, the conductor 111A has a substantially tubular shape. The outer conductors 111A and the inner conductors 111B may be formed, for example, of aluminum, stainless steel, brass, copper, other metals, coated metals, metal-coated plastic, metal alloys, combinations thereof, or any other suitable conductive material. Although other configurations are possible, FIG. 1 shows that the inner conductor 111B may be recessed within the outer conductor 111A to partially accommodate the shape of the cornea 2.

With the concentric arrangement of conductors 111A and 111B, a substantially annular gap 111C of a selected distance is defined between the conductors 111A and 111B. The annular gap 111C extends from the proximal end 110A to the distal end 110B. A dielectric material 111D may be used in portions of the annular gap 111C to separate the conductors 111A and 111B. The distance of the annular gap 111C between conductors 111A and 111B determines, in part, the penetration depth of microwave energy into the cornea 2 according to established microwave field theory. Thus, the energy conducting element 111 receives, at the proximal end 110A, the electrical energy generated by the electrical energy source 120, and directs microwave energy to the distal end 110B, where the cornea 2 is positioned.

In general, the outer diameter of the inner conductor 111B may be selected to achieve an appropriate change in corneal shape, i.e. keratometry, induced by the exposure to microwave energy. Meanwhile, the inner diameter of the outer conductor 111A may be selected to achieve a desired gap between the conductors 111A and 111B. For example, the outer diameter of the inner conductor 111B ranges from about 2 mm to about 10 mm while the inner diameter of the outer conductor 111A ranges from about 2.1 mm to about 12 mm. In some systems, the annular gap 111C may be sufficiently small, e.g., in a range of about 0.1 mm to about 2.0 mm, to minimize exposure of the endothelial layer of the cornea (posterior surface) to elevated temperatures during the application of energy by the applicator 110.

A controller 140 may be employed to selectively apply the energy in the form of heat any number of times according to any predetermined or calculated sequence. In addition, the heat may be applied for any length of time. Furthermore, the magnitude of heat being applied to the cornea may also be varied. Adjusting such parameters for the application of heat determines the extent of changes that are brought about within the cornea 2. Of course, the system attempts to limit the changes in the cornea 2 to an appropriate amount of shrinkage of collagen fibrils in a selected region and according to a selected pattern. When employing microwave energy to generate heat in the cornea 2, for example with the applicator 110, the microwave energy may be applied with low power (e.g., of the order of 40 W) and in long pulse lengths (e.g., of the order of one second). However, other systems may apply the microwave energy in short pulses. In particular, it may be advantageous to apply the microwave energy with durations that are shorter than the thermal diffusion time in the cornea 2. For example, the microwave energy may be applied in pulses having a higher power in the range of about 500 W to about 3 kW and a pulse duration in the range of about 5 milliseconds to about one second.

Referring again to FIG. 1, at least a portion of each of the conductors 111A and 111B may be coated or covered with an electrical insulator to minimize the concentration of electrical current in the area of contact between the corneal surface (epithelium) 2A and the conductors 111A and 111B. In some systems, the conductors 111A and 111B, or at least a portion thereof, may be coated or covered with a material that can function both as an electrical insulator as well as a thermal conductor.

In the system illustrated in FIG. 1, a dielectric layer 110D is disposed along the distal end 111B of the applicator 110 to protect the cornea 2 from electrical conduction current that would otherwise flow into the cornea 2 via conductors 111A and 111B. Such current flow may cause unwanted temperature effects in the cornea 2 and interfere with achieving a maximum temperature within the collagen fibrils in a mid-depth region 2B of the cornea 2. Accordingly, the dielectric layer 110D is positioned between the conductors 111A and 111B and the cornea 2. The dielectric layer 110D may be sufficiently thin to minimize interference with microwave emissions and thick enough to prevent superficial deposition of electrical energy by flow of conduction current. For example, the dielectric layer 110D may be a biocompatible material deposited to a thickness of about 20-100 micrometers, preferably about 50 micrometers. As another example, the dielectric layer 110D can be a flexible sheath-like structure of biocompatible material that covers the conductors 111A and 111B at the distal end 110B and extends over a portion of the exterior wall of the outer conductor 111B. As still a further example, the dielectric layer 110D can include a first flexible sheath-like structure of biocompatible material that covers the distal end of the inner conductor 111A and a second flexible sheath-like structure of biocompatible material that covers the distal end of the outer conductor 111B.

In general, an interposing layer, such as the dielectric layer 110D, may be employed between the conductors 111A and 111B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. The dielectric material may be elastic (e.g., polyurethane, silastic, combinations thereof and/or the like) or nonelastic (e.g., Teflon®, polyimides, combinations thereof and/or the like). The dielectric material may have a fixed dielectric constant or varying dielectric constant by mixing materials or doping the sheet, the variable dielectric being spatially distributed so that it may affect the microwave hearing pattern in a customized way. The thermal conductivity of the material may have fixed thermal properties (e.g., thermal conductivity and/or specific heat), or may also vary spatially, through mixing of materials or doping, and thus provide a means to alter the heating pattern in a prescribed manner. Another approach for spatially changing the heating pattern is to make the dielectric sheet material of variable thickness. The thicker region will heat less than the thinner region and provides a further means of spatial distribution of microwave heating.

During operation, the distal end 110B of the applicator 110 as shown in FIG. 1 is positioned on or near the corneal surface 2A. Preferably, the applicator 110 makes direct contact with the corneal surface 2A. In particular, such direct contact positions the conductors 111A and 111B at the corneal surface 2A (or substantially near the corneal surface 2A if there is a thin interposing layer between the conductors 111A and 111B and the corneal surface 2A). Accordingly, direct contact helps ensure that the pattern of microwave heating in the corneal tissue has substantially the same shape and dimension as the gap 111C between the two microwave conductors 111A and 111B.

The system of FIG. 1 is provided for illustrative purposes only, and other systems may be employed to apply heat to cause reshaping of the cornea. Other systems are described, for example, in U.S. patent application Ser. No. 12/208,963, filed Sep. 11, 2008, which is a continuation-in-part application of U.S. patent application Ser. No. 11/898,189, filed on Sep. 10, 2007, the contents of these applications being entirely incorporated herein by reference. As described in U.S. patent application Ser. No. 12/208,963, a cooling system may also be employed in combination with the applicator 110 to apply coolant to the cornea 2 and determine how the energy is applied to the cornea 2.

Figure 2A:
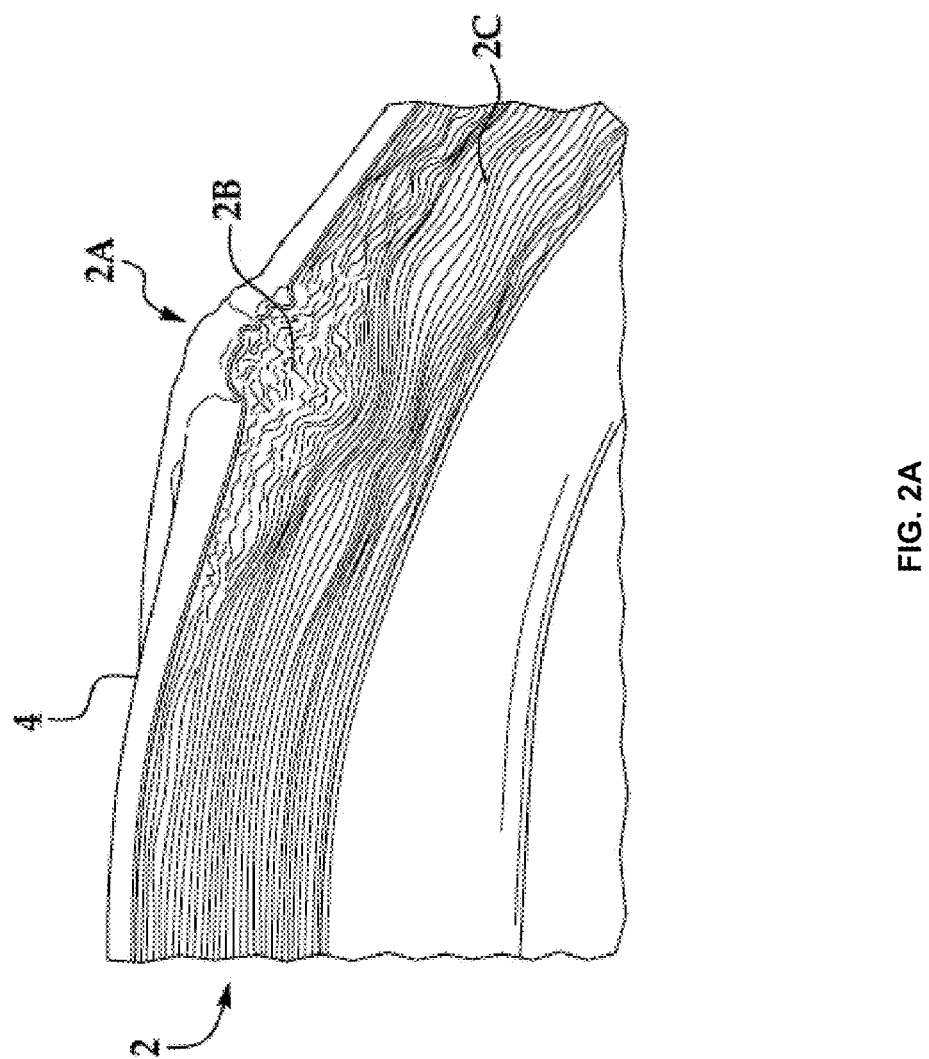
FIG. 2A illustrates a high resolution image of a cornea after heat has been applied.
Figure 2B:
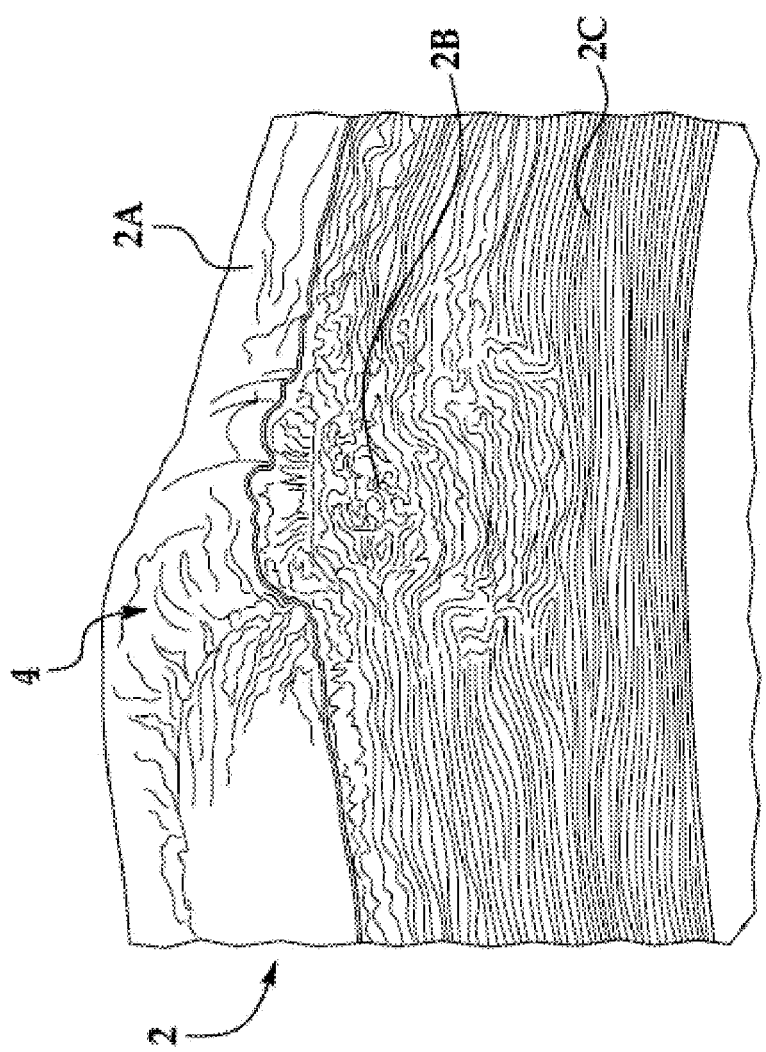
FIG. 2B illustrates another high resolution image of the cornea of FIG. 2A.

FIGS. 2A-D illustrate an example of the effect of applying heat to corneal tissue with a system for applying heat, such as the system illustrated in FIG. 1. In particular, FIGS. 2A and 2B illustrate high resolution images of cornea 2 after heat has been applied. As FIGS. 2A and 2B show, a lesion 4 extends from the corneal surface 2A to a mid-depth region 2B in the corneal stroma 2C. The lesion 4 is the result of changes in corneal structure induced by the application of heat as described above. These changes in structure result in an overall reshaping of the cornea 2. It is noted that the application of heat, however, has not resulted in heat-related damage to the corneal tissue.

Figure 2C:
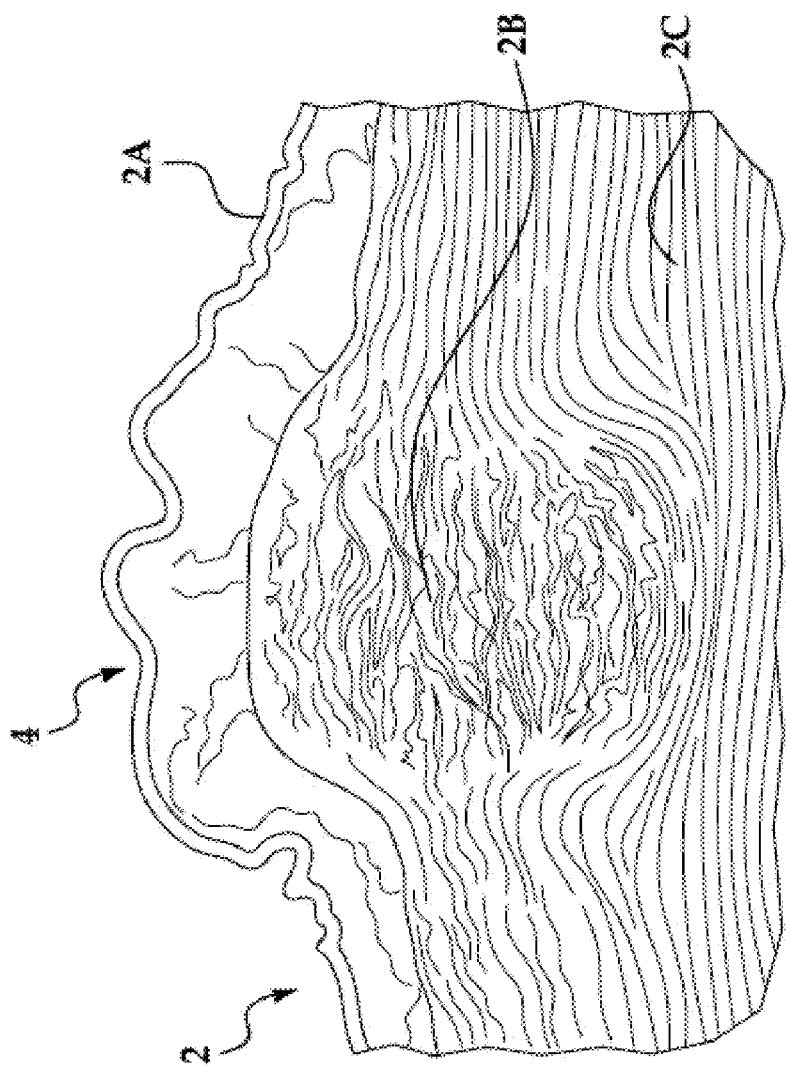
FIG. 2C illustrates a histology image of the cornea of FIG. 2A.
Figure 2D:
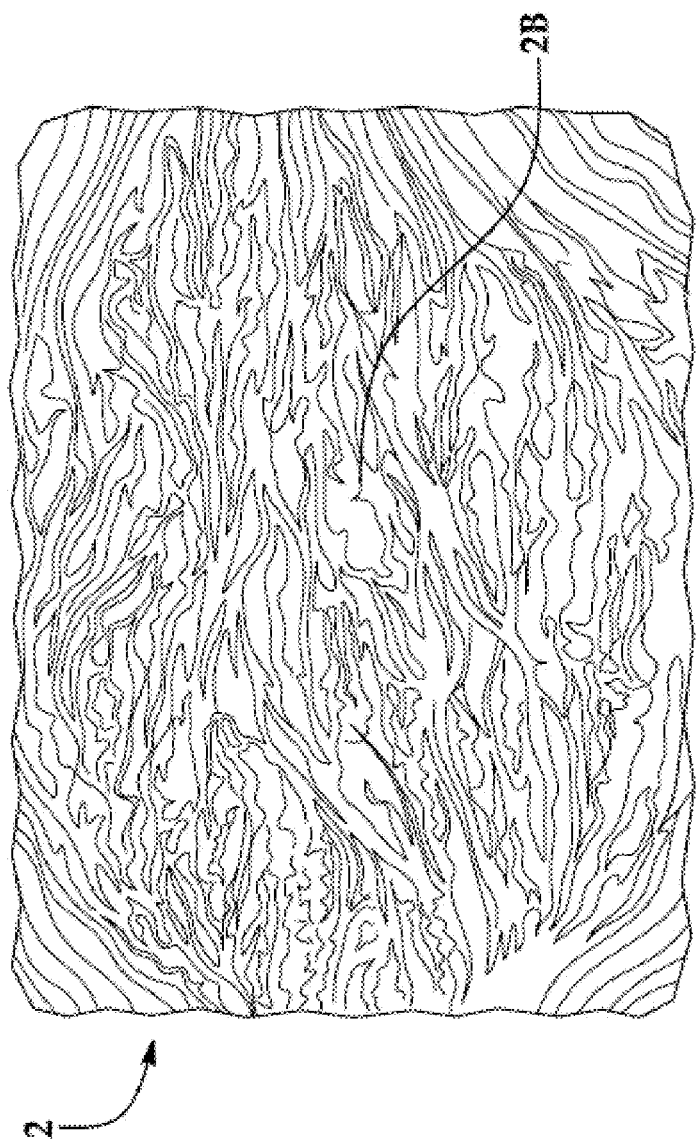
FIG. 2D illustrates another histology image of the cornea of FIG. 2A.
Figure 4B:
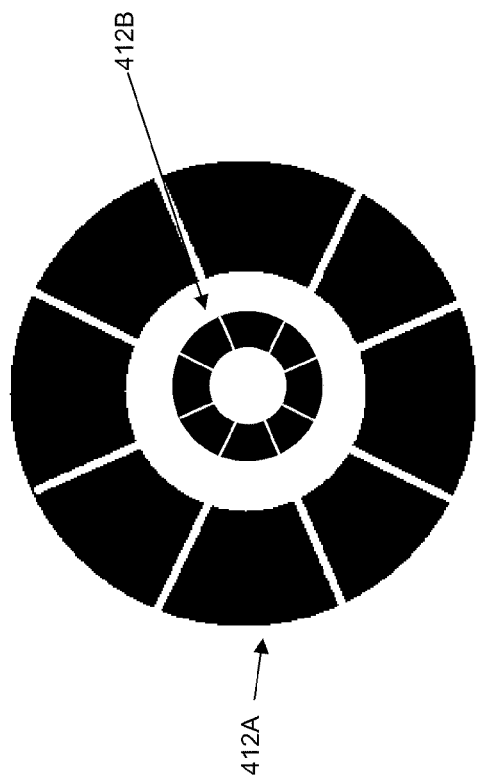
FIG. 4B illustrates a view of an energy conducting element according to still further aspects of the present invention.
Figure 4A:
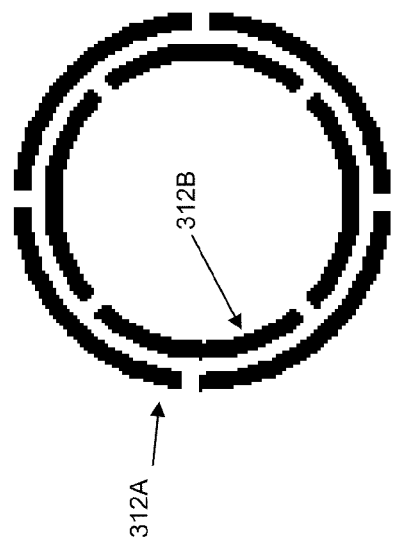
FIG. 4A illustrates a view of an energy conducting element according further aspects of the present invention.
Figure 4D:
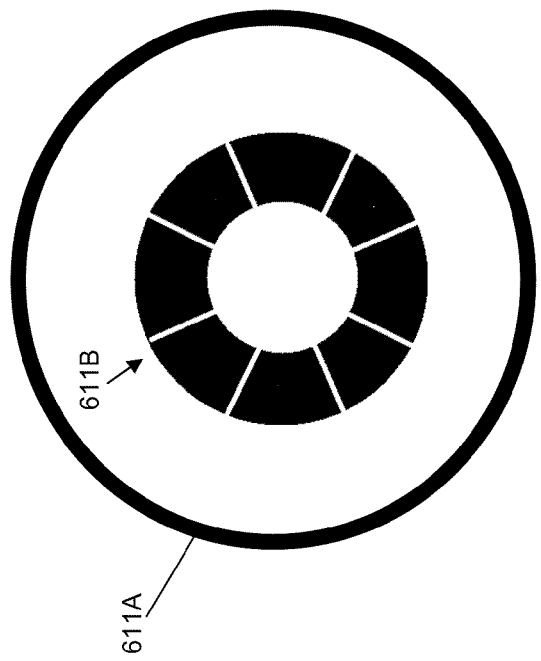
FIG. 4D illustrates a view of an energy conducting element according to still further aspects of the present invention.
Figure 4C:
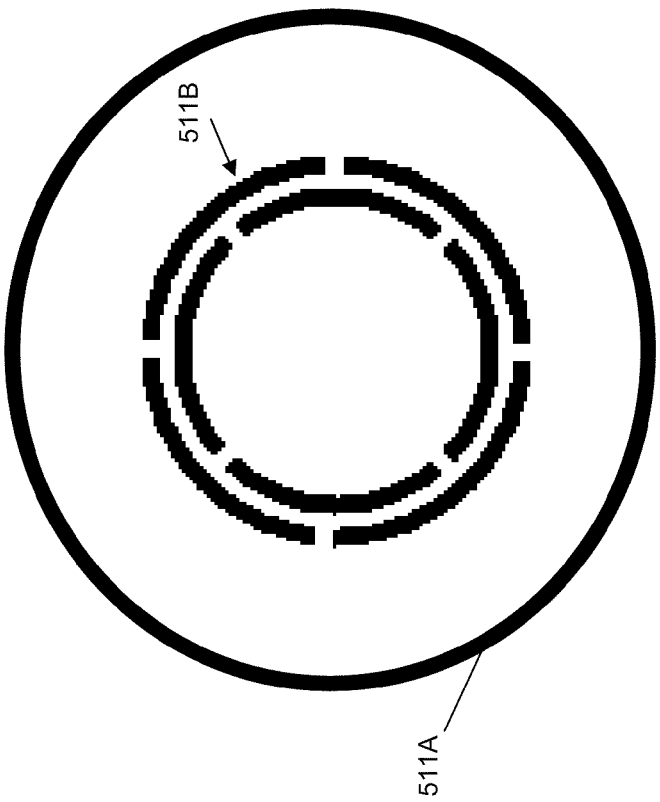
FIG. 4C illustrates a view of an energy conducting element according to still further aspects of the present invention.

As further illustrated in FIGS. 2A and 2B, the changes in corneal structure are localized and limited to an area and a depth specifically determined by an applicator as described above. FIGS. 2C and 2D illustrate histology images in which the tissue shown in FIGS. 2A and 2B has been stained to highlight the structural changes induced by the heat. In particular, the difference between the structure of collagen fibrils in the mid-depth region 2B where heat has penetrated and the structure of collagen fibrils outside the region 2B is clearly visible. Thus, the collagen fibrils outside the region 2B remain generally unaffected by the application of heat, while the collagen fibrils inside the region 2B have been rearranged and formed new bonds to create completely different structures. In other words, unlike processes, such as orthokeratology, which compress areas of the cornea to reshape the cornea via mechanical deformation, the collagen fibrils in the region 2B are in an entirely new state.

As shown in FIG. 1, the energy conducting element 111 includes a contact surface 111G at the distal end 110B of the outer conductor 111A and a contact surface 111H at the distal end 110B of the inner conductor 111B. The contact surfaces 111G and 111H, or portions thereof, come into direct contact with the corneal surface 2A. In general, the pattern of energy applied to the cornea 2 depends in part on the position of the contact surfaces 111G and 111H relative to the corneal surface 2A. The contact surfaces 111G and 111H are shown to be contoured in FIG. 1, but it is understood that the contact surfaces 111G and 111H may have other predetermined shapes.

Although the contact surfaces 111G and 111H may be designed to have a contoured shape, this predetermined shape may not correspond sufficiently to the actual shape of the corneal surface 2A. Moreover, the contact surfaces 111G and 111H may be formed as integral surfaces from a rigid material, so that they cannot be dynamically changed to correspond more closely to the actual shape of the corneal surface 2A. In general, the cost of providing a customized applicator, such as the applicator 110 in FIG. 1, for each individual application may be prohibitive, so the contact surface 111G and 111H may be designed to approximate the general shape of the corneal surface 2A as best as possible and to offer the broadest possible use. For example, the contact surfaces 111G and 111H may each be a single surface shaped according to a symmetric concave model of the cornea 2. Because the actual shapes of corneal surfaces 2A may vary according to different individuals, however, the contact surfaces 111G and 111H may not provide the desired contact between the energy conducting element 111 and the corneal surface 2A. In some cases, individuals may have asymmetric corneas 2 which are likely to experience non-uniform contact when symmetric contact surfaces 111G and 111H are applied. Non-uniform contact may result in imprecise and inaccurate delivery of energy to the cornea 2 and may prevent the desired reshaping of the cornea 2.

Furthermore, in some cases, the energy conducting element 111 is applied to the corneal surface 2A to cause an observable amount of flattening, or applanation, of the cornea 2. Although applanation may provide a good indication that contact between the contact surfaces 111G and 111H and the corneal surface 2A has been achieved, pressure applied by the contact surfaces 111G and 111H may be non-uniform over the contact surfaces 111G and 111H if the shape of the contact surfaces 111G and 111H does not correspond sufficiently with the corneal surface 2A. The application of non-uniform pressure against the corneal surface 2A may produce mechanical deformation that may affect the results of thermokeratoplasty.

Systems and methods for causing applanation of the cornea are described in U.S. patent application Ser. No. 12/209,123, filed Sep. 11, 2008, which is a continuation-in-part application of U.S. patent application Ser. No. 12/018,457, filed on Jan. 23, 2008, and U.S. Provisional Patent Application No. 61/113,395, filed Nov. 11, 2008, the contents of these applications being entirely incorporated herein by reference. In addition, the effects of mechanical deformation during thermokeratoplasty are described, for example, in U.S. application Ser. No. 12/018,473, filed Jan. 23, 2008, the contents of which are entirely incorporated herein by reference.

To achieve a desired application of energy to the cornea, aspects of the present invention account for the shape of the cornea when the applicator is positioned to deliver energy. In particular, an energy conducting element of the applicator includes a plurality of movable segments that can adjust to the shape of the cornea when positioned against the cornea. The plurality of movable segments defines a total contact surface that corresponds to the shape of the cornea and provides the desired contact for the delivery of energy. Advantageously, the ability to adjust the shape of the total contact surface dynamically allows a single applicator design to be employed on varying corneal shapes.

FIGS. 3A-C illustrate an embodiment of an applicator 210 with an energy conducting element 211 that provides adjustable contact with the cornea 2 of an eye 1. Like the energy conducting element 111, the energy conducting element 211 includes an outer conductor 211A and an inner conductor 211B that extend along a longitudinal axis 210C from a proximal end 210A to a distal end 210B. However, the outer conductor 211A is defined at the distal end 210B by a plurality of outer conductor segments 212A, and the inner conductor 211B is defined at the distal end 210B by a plurality of inner conductor segments 212B. In other words, unlike the outer conductor 111A and the inner conductor 111B in FIG. 1, the outer conductor 211A and the inner conductor 211B are each configured to contact the corneal surface 2A with more than one component.

As shown in FIG. 3A, the segments 212A and 212B may extend along the longitudinal axis 210C from an intermediate section 210D of the energy conducting element 211 to the distal end 210B. In addition, as FIG. 3B illustrates, the outer conductor segments 212A may be organized within a region bounded by dashed lines A, which might generally correspond with the exterior walls of the outer conductor 111A of FIG. 1. Similarly, the inner conductor segments 212B may be organized within a region bounded by dashed line B, which might generally correspond with the exterior walls of the inner conductor 111B of FIG. 1. In the example embodiment of FIGS. 3A-C, the segments 212A and 212B may be formed as cylindrical or pin-like structures from electrically conducting materials.

Like the conductors 111A and 111B, aspects of the conductors 211A and 211B may be formed, for example, from aluminum, stainless steel, brass, copper, other metals, coated metals, metal-coated plastic, other metal alloys, combinations thereof or any other suitable conductive material. Although a specific number of segments 212A and 212B may be illustrated, it is contemplated that any number of segments 212A and 212B may be employed as long as the configuration provides the appropriate conducting characteristics for delivering energy to the cornea 2.

Each of the segments 212A includes a segment contact surface 212C, and each of the segments 212B includes a segment contact surface 212D. Collectively, the segment contact surfaces 212C define a total contact surface 211G for the outer conductor 211A, while the segment contact surfaces 212D define a total contact surface 211H for the inner conductor 211B. The total contact surfaces 211G and 211H at the distal end 210B of the outer conductor 211A and the inner conductor 211B, respectively, contact the corneal surface 2A to deliver the energy to the cornea 2.

As explained above, in some systems, the conductors 211A and 211B, or at least a portion thereof, may be coated with or covered by a material that can function both as an electrical insulator as well as a thermal conductor. The material may be a dielectric layer employed along the distal end 210B of the applicator 210 to protect the cornea 2 from electrical conduction current that would otherwise flow into the cornea 2 via conductors 211A and 211B. The dielectric layer may be employed between the conductors 211A and 211B and the cornea 2 as long as the interposing layer does not substantially interfere with the strength and penetration of the microwave radiation field in the cornea 2 and does not prevent sufficient penetration of the microwave field and generation of a desired heating pattern in the cornea 2. As an example, the dielectric layer can be a flexible sheath-like structure of biocompatible material that covers the conductors 211A and 211B at the distal end 210B and extends over a portion of the exterior wall of the outer conductor 211B. As another example, the dielectric layer can include a first flexible sheath-like structure of biocompatible material that covers the distal end of the inner conductor 211A and a second flexible sheath-like structure of biocompatible material that covers the distal end of the outer conductor 211B. As still a further example, the dielectric layer can be formed as a plurality of sheath-like structures that are individually positioned over the outer surface of each of the conductor segments 212A and 212B.

As shown in FIGS. 3A-C, the segments 212A and 212B may be spaced apart from each other. However, the proximity of the segments 212A allows the segments 212A collectively to act as a single outer conductor, and the proximity of the segments 212B allows the segments 212B collectively to act as a single inner conductor. In particular, the segments 212A may be arranged so that the effect of delivering energy through one segment 212A extends across the spaces to adjacent segments 212A, and the segments 212B are arranged so that the effect of delivering energy through one segment 212B extends across the spaces to adjacent segments 212B.

Thus, the combination of the outer conductor 211A and the inner conductor 211B delivers energy from an energy source 220 to a distal end 210B. As described previously, the energy is delivered to the cornea 2 in a pattern that depends, in part, on a gap 211C at the distal end 210B defined between the outer conductor 211A and the inner conductor 211B. In general, the energy conducting element 211 may be applied to the eye 1 in a manner similar to the energy conducting element 111 to generate heat and cause reshaping of the cornea 2.

However, as illustrated in FIG. 3C, each outer conductor segment 212A can move along the longitudinal axis 210C, relative to each of the other outer conductor segments 212A. Similarly, each inner conductor segment 212B can move along the longitudinal axis 210C, relative to each of the other inner conductor segments 212B. Thus, unlike the statically shaped contact surfaces 111G and 111H shown in FIG. 1, the segments 212A and 212B are movable to define different shapes for total contact surfaces 211G and 211H, respectively. As shown in FIG. 3A, the segments 212A and 212B may be moved so that the total contact surfaces 211G and 211H fit the actual shape of the corneal surface 2A more closely.

In addition, FIGS. 3A and 3C show that the applicator 210 may employ biasing devices 211K and 211L that provide a slight bias in the +x direction against corresponding segments 212A and 212B. For example, the biasing devices 211K and 211L may be springs or a material with spring-like characteristics. In general, the biasing devices 211K and 211L provide a force in the +x direction according to a displacement in the −x direction (i.e., F=−kx, where F is the restoring force exerted by the biasing device in the +x direction, x is the displacement from equilibrium in the −x direction, and k is a force constant). Although gravity may be employed to force the segments 212A and 212B in the +x direction into contact with the cornea 2, the biasing devices 211K and 211L may additionally or alternatively be employed to provide a force in the +x direction. The biasing devices 211K and 211L ensure that the segments 212A and 212B remain in contact with the corneal surface 2A without creating an undesired level of pressure against the corneal surface 2A that may affect the thermokeratoplasty. To reduce the risk of an undesired level of pressure against the corneal surface 2A, the inner conductor segments 212B may be recessed within the outer conductor segments 212A (i.e., the inner conductor segments 212B may be shorter than the outer conductor segments 212A) or the biasing devices 211K and 211L may be configured such that the biasing force applied to the outer segments 212A is greater than the biasing force applied to the inner segments 212B. As further illustrated by FIGS. 3A and 3C, the biasing devices 211K and 211L may be employed in combination with the couplings 211I and 211J, respectively, where they can act on the ends of the corresponding segments 212A and 212B.

According to some embodiments, the applicator 210 can also include one or more devices for determining whether sufficient contact has been established between the applicator 210 (i.e., the individual conductor segments 212A and 212B) and the eye for accurate and precise delivery of energy to the eye. Such devices are described in U.S. application Ser. No. 12/617,544, filed Nov. 12, 2009, the contents of which being entirely incorporated herein by reference.

In operation, the energy conducting element 211 is moved in the +x direction to position each of the segments 212A and 212B against the corneal surface 2A. During this process, some segments 212A and 212B may come into contact with the corneal surface 2A, while the other segments 212A and 212B require further movement of the energy conducting element 211 in the +x direction to reach the corneal surface 2A. For example, as shown in FIG. 3A, the inner conductor segments 212B may reach the corneal surface 2A before the outer conductor segments 212A, because the central region of the cornea 2 extends farther from the rest of the eye 1 and toward the oncoming energy conducting element 211. As the energy conducting element 211 continues to move toward the cornea 2, the corneal surface 2A applies a reaction force against the segments 212A and 212B already in contact. This reaction force causes the corresponding segments 212A and 212B to move in the −x direction, i.e., opposite to the other segments 212A that are not in contact with the corneal surface 2A and that are still moving toward the corneal surface 2A. Although there may be a bias acting on the segments 212A and 212B in the +x direction, the reaction force in the −x direction is able to overcome the bias and cause movement of the segments 212A and 212B. As discussed previously, this bias promotes contact between the corneal surface 2A and the segments 212A and 212B, but does not apply undesired levels of pressure as the segments 212A and 212B move against the bias. The energy conducting element 211 is moved until all the segments 212A and 212B are in contact with the corneal surface 2A. The relative movement between the segments 212A and 212B allows the total contact surfaces 211G and 211H to change according to the shape of the corneal surface 2A. Moreover, the relative movement allows the contact and pressure applied by the energy conducting element 211 to be more uniform. Accordingly, as illustrated by the embodiment of FIGS. 3A-C, aspects of the present invention provide a self-adjusting applicator that promotes desired contact with more uniform pressure. Once the appropriate contact has been achieved between the total contact surfaces 211G and 211H and the corneal surface 2A, energy can be delivered, via the conductors 211A and 211B, to the cornea 2 in the desired reshaping pattern.

As shown further in FIGS. 3A and 3C, the segments 212A extend from the distal end 210B to the intermediate section 210D of the outer conductor 211A where they may be electrically connected by a coupling 211I. Likewise, the segments 212B extend from the distal end 210B to the intermediate section 210D of the inner conductor 211B where they may be electrically connected by a coupling 211J. The couplings 211I and 211J may be formed of a conductive material, such as those described previously, and facilitate the delivery of energy from the energy source 220 to the segments 212A and 212B, respectively. When moving along the longitudinal axis 210C, the segments 212A and 212B may, for example, slide within openings in the corresponding couplings 211I and 211J while remaining in conductive contact with the couplings 211I and 211J. Alternatively, 211I or 2121J may be flexible and may bend as the segments 212A or 212B slide up or down.

There are significant additional advantages to having multiple, individually adjustable outer conductor segments 212A and/or inner conductor segments 212B. In particular, a system including multiple, individually adjustable outer conductor segments 212A and/or inner conductor segments 212B can be selectively configured by raising and/or lowering the individual segments 212A and 212B to provide energy to the cornea 2 according to a desired penetration depth and/or pattern.

The penetration depth of the energy into the cornea 2 is determined, in part, by the distance of the gap 211C between the outer conductor 211A and the inner conductor 211B. If, for example, the inner row of segments 212A of the outer conductor 211A is raised and no longer makes direct contact with the cornea surface 2A, only the outer ring of segments 212A of the outer conductor 211A will be in contact with the cornea surface 2A and the gap 211C will be widened between the inner conductor 211B and outer conductor 211A at or near the cornea surface 2A. Similarly, if the outer row(s) of segments 212B of the inner conductor 211B is raised and no longer makes direct contact with the cornea surface 2A, only the inner ring(s) of segments 212B of the inner conductor 211B will be in contact with the cornea surface 2A and the gap 211C will also be widened between the inner conductor 211B and the outer conductor 211A at or near the cornea surface 2A. This variation in the distance of the gap 211C affects the penetration depth of microwave energy into the cornea 2, influencing the resulting lesion. Accordingly, the distance of the gap 211C (and thus the penetration depth) can be controlled by selectively raising one or more of the inner rows of the outer conductor segments 212A and/or one or more of the outer rows of the inner conductor segments 212B.

While FIGS. 3A-3C illustrate the outer conductor 211A having two rows of outer conductor segments 212A and the inner conductor 211B having six rows of inner conductor segments 212B, any other number of rows of outer conductor segments 212A or inner conductor segments 212B can be provided. The greater the number of rows of segments 212A and 212B provided, the greater the flexibility provided for selection of the distance of the gap 211C.

The pattern of energy applied to the cornea 2 is determined, in part, by the contact surfaces 211G and 211H at or near the cornea surface 2A. By selectively controlling the elevation of the individual segments 212A and 212B relative to the cornea surface 2A, various effective contact surface 211G and 211H configurations can be achieved.

For example, if only the outer ring of conductor segments 212B of the inner conductor 211B is in contact with the cornea surface 2A, the heating pattern will be based on a ring shaped inner conductor. If a smaller ring of conductor segments 212B is left in contact with the cornea surface 2A due to the elevation of the remaining conductor segments 212B, the heating zone will be a smaller ring.

As another example, if some part of the circumference (e.g., 90-180°) of the outer conductor 211A is raised and no longer contacts cornea surface 2A (i.e., both the inner row and the outer row of the outer conductor segments 212A are raised at a part of the circumference), the heating zone will be biased away from the noncontact region.

As still another example, if only one to ten individual, non-neighbor, conductor segments 212B of the inner conductor 211B are lowered onto the cornea surface, individual spot treatments due to the individual conductor contact will result. And if, for example, two to five neighbor conductor segments 212B are lowered into contact with the cornea, a larger, well-defined region will be treated. Such spot treatments may be useful to treat particular disorders such as, for example, astigmatism.

Additional examples of non-annular energy patterns, which may be formed by the conductor segments 212A and 212B are described in U.S. patent application Ser. No. 12/113,672, filed on May 1, 2008, the contents of which is entirely incorporated herein by reference.

To achieve various configurations of the outer conductor segments 212A and the inner conductor segments 212B, electrical and/or mechanical devices may be employed to raise, lower, and/or lock individual conductor segments 212A and 212B at various elevations relative to the cornea surface 2A. For example, each conductor segment 212A and 212B can be coupled to an actuator device in addition to or instead of the biasing devices described above. The actuator devices can be any devices capable of moving conductor segments 212A and 212B in the −x and/or +x direction along the longitudinal axis 210C. Nonlimiting examples of suitable actuator devices include electrical motors, pneumatic actuators, hydraulic pistons, relays, electroactive polymers, combinations thereof, and/or any other transducer device. The actuator devices can be further coupled to a controller for providing automated control of the elevation of the segments 212A and 212B relative to the cornea surface 2A. Optionally, a locking mechanism can be employed to ensure that the segments 212A and 212B are locked at a specific elevation relative to the cornea surface 2A after the actuator device has moved the segments 212A and 212B into the appropriate position.

According to one embodiment, a particular configuration of the conductor segments 212A and 212B can be achieved by first moving all segments 212A and 212B into contact with the cornea surface 2A to achieve uniform pressure as described above and then raising specific segments 212A and 212B to one or more elevations above the cornea surface 2A. Alternatively, a particular configuration of conductor segments 212A and 212B can be achieved by first moving specific segments 212A and 212B to one or more raised positions and then moving the remaining segments 212A and 212B into contact with the cornea surface 2A to achieve uniform pressure over the remaining segments 212A and 212B.

There are still further advantages to a system having multiple outer conductor segments 212A and inner conductor segments 212B. For example, a system having multiple outer conductor segments 212A and inner conductor segments 212B also advantageously allows for selective application of energy through the individual segments 212A and/or 212B to the cornea 2. In other words, energy can be applied to the cornea 2 by some segments 212A and 212B but not other segments 212A and 212B. Accordingly, the depth of penetration can be selectively configured by activating or deactivating conductor segments 212A and 212B to achieve a selected distance for the gap 211C. Likewise, a pattern of energy applied to the cornea can be selectively configured by activating or deactivating the individual segments 212A and 212B.

To selectively apply energy to individual segments 212A and/or 212B, each of the segments 212A and 212B is individually coupled to the energy source 220. In operation, electrical energy from the energy source 220 can be conducted from the proximal end 210A to the distal end 210B via the outer conductor segments 212A and inner conductor segments 212B that are activated. According to some embodiments, a controller can be employed to select and activate the conductor segments 212A and 212B. Additionally, a dielectric material may be disposed between neighbor (i.e., adjacent) segments to prevent or inhibit conduction of electrical current between the conductors 212A and 212B. In some embodiments, the dielectric material may be formed as a part of sheath-like structures positioned over the outer surface of the conductors 212A-B.

Additional details and advantages associated with selectively activating and deactivating particular segments 212A and 212B are described in a U.S. Non-Provisional Application that is being concurrently filed, which claims the benefit of priority from U.S. Provisional Application No. 61/166,009, filed Apr. 2, 2009, the entire contents of which are hereby incorporated by reference.

It is contemplated that each conductor segment 212A and/or 212B can be activated/deactivated when positioned in an elevated position relative to the cornea surface 2A, or when positioned in contact with the cornea surface 2A. Thus, the depth of penetration and/or the pattern of energy applied to the cornea can be controlled by selectively configuring the elevation of the conductor segments 212A and 212B and/or selectively activating or deactivating the conductor segments 212A and 212B.

Accordingly, the applicator 210 provides a single convenient and versatile tool that allows an operator to apply energy to the cornea according to different patterns and different penetration depths to suit different treatment cases, without requiring multiple applicators or interchangeable components. Although the applicator 210 may be employed for a single application of energy according to a single outer conductor/inner conductor pair, the applicator 210 may be particularly advantageous when multiple applications of energy according to multiple patterns are required to achieve the desired change in the shape of the cornea. For example, energy is incrementally applied to the cornea in precise and measured steps in multiple ring-shaped patterns. An example of a multi-step approach is described in U.S. patent application Ser. No. 61/098,489, filed on Sep. 19, 2008, the contents of which are entirely incorporated herein by reference. In general, energy may be applied multiple times according to different patterns and pulses, i.e., duration and magnitude, to achieve the desired shape change. Indeed, in some embodiments, an asymmetric shape change, for example to treat astigmatism, may be effected by multiple applications of energy in different ring-shaped patterns that are centered at different areas of the cornea.

While the conductor segments 212A and 212B illustrated in FIGS. 3A-3C were formed as cylindrical or pin-like structures, it is contemplated that in other embodiments, the segments can have any suitable shape or size. For example, according to the alternative embodiments illustrated in FIGS. 4A-D, the conductors 311A-B, 411A-B, 511B and 611B may include segments that are formed as discrete sectors or sections of a cylinder. It is further contemplated that in some embodiments, the segments may include a combination of different shapes and sizes.

Although embodiments above may refer to one energy source and to one controller, it is understood that more than one respective energy source and/or more than one controller may be employed to operate an applicator according to aspects of the present invention. For example, referring to the embodiment of FIG. 3, each of the conductor segments 212A-B may be coupled to a dedicated energy source. The conductors segments 212A-B and their respective energy sources may be selectively activated by one controller. Alternatively, each of the conductors segments 212A-B may each be selectively activated by a dedicated controller. In general, any number of conductors or conductor segments may be coupled to any number of energy sources and any number of controllers to deliver an appropriate amount energy for an appropriate duration according to a desired pattern.

Furthermore, the controller(s) described above may be a programmable processing device that executes software, or stored instructions, and that may be operably connected to the other devices described above. In general, physical processors and/or machines employed by embodiments of the present invention for any processing or evaluation may include one or more networked or non-networked general purpose computer systems, microprocessors, field programmable gate arrays (FPGAs), digital signal processors (DSPs), micro-controllers, and the like, programmed according to the teachings of the exemplary embodiments of the present invention, as is appreciated by those skilled in the computer and software arts. The physical processors and/or machines may be externally networked with the image capture device, or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits (ASICs) or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the exemplary embodiments of the present invention may include software for controlling the devices and subsystems of the exemplary embodiments, for driving the devices and subsystems of the exemplary embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present inventions can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

Although the embodiments described above are applied to a cornea, other embodiments may be applied to other features of an eye.

While the present invention has been described in connection with a number of exemplary embodiments, and implementations, the present inventions are not so limited, but rather cover various modifications, and equivalent arrangements.

We claim:

1. A system for applying thermokeratoplasty to an eye, the system comprising:
   an electrical energy source; and
   an electrical energy conducting element extending from a proximal end to a distal end, the energy conducting element electrically connected to the electrical energy source at the proximal end, the energy conducting element including:
      an outer conductor extending to the distal end, the outer conductor including a plurality of moveable outer segments; and
      an inner conductor extending to the distal end and disposed within the outer conductor, the inner conductor including a plurality of moveable inner segments, the outer conductor and the inner conductor being separated by a gap, the plurality of outer segments and the plurality of inner segments forming a total contact surface at the distal end, the total contact surface being positionable at a corneal surface of an eye such that an energy is applied to the eye according to the total contact surface to cause shrinkage of corneal tissue of the eye in response to the electrical connection between the energy conducting element and the electrical energy source,
   wherein each of the plurality of outer segments is individually and separately moveable and each of the plurality of inner segments is individually and separately moveable.

2. The system of claim 1, wherein the total contact surface corresponds to the shape of a cornea.

3. The system of claim 1, wherein the plurality of outer segments and the plurality of inner segments are operable to adjust to the shape of the eye.

4. The system of claim 1, wherein the plurality of outer segments and the plurality of inner segments extend from an intermediate section of the conducting element to the distal end, the intermediate section being between the proximal end and the distal end.

5. The system of claim 4, wherein the plurality of outer conductors and the plurality of inner conductors are connected to the intermediate section by one or more coupling devices.

6. The system of claim 1 further comprising at least one biasing member, the at least one biasing member biasing the plurality of outer segments and the plurality of inner segments towards the distal end.

7. The system of claim 1, wherein the plurality of outer segments and the plurality of inner segments are substantially cylindrical at the distal end.

8. The system of claim 1, wherein the plurality of outer segments and the plurality of inner segments are moveable between the proximal end and the distal end.

9. The system of claim 1, wherein at least one of the outer segments and at least one of the inner segments are operable to be fixed at one or more positions between the proximal end and the distal end.

10. The system of claim 9, wherein the position at which the at least one outer segment and the at least one inner segment are fixed is dependent upon a pattern of energy to be applied to the eye.

11. The system of claim 10, wherein the pattern is asymmetric.

12. The system of claim 9, wherein the position at which the at least one outer segment and the at least one inner segment are fixed is dependent upon a selected depth of penetration of the energy to be applied to the eye.

13. The system of claim 1, wherein the gap is a substantially annular gap.

14. The system of claim 1 further comprising a controller configured to control the supply of electrical energy to each outer segment and each inner segment, each outer segment and each inner segment being individually coupled to the electrical energy source.

15. The system of claim 1, wherein each outer segment is spaced apart from each adjacent outer segment such that the plurality of outer segments collectively act as a single outer conductor and each inner segment is spaced apart from each adjacent inner segment such that the plurality of inner segments collectively act as a single inner conductor.

16. The system of claim 1 further comprising a layer of dielectric material disposed on at least a portion of the total contact surface, the layer of dielectric material being configured to substantially inhibit an electrical current from the inner conductor and the outer conductor into the corneal tissue while allowing a microwave heating pattern to be applied to the eye according to the total contact surface to cause shrinkage of corneal tissue of the eye in response to the electrical connection between the energy conducting element and the electrical energy source.

17. A method for applying thermokeratoplasty to an eye, the method comprising:
positioning a total contact surface of an electrical energy conducting element at a corneal surface of an eye, the energy conducting element being operably connected to an electrical energy source at a proximal end and extending to the total contact surface at a distal end, the energy conducting element including:
an outer conductor extending to the distal end, the outer conductor including a plurality of moveable outer segments; and
an inner conductor extending to the distal end and disposed within the outer conductor, the inner conductor including a plurality of moveable inner segments, the outer conductor and the inner conductor being separated by a gap, the plurality of outer segments and the plurality of inner segments forming the total contact surface at the distal end; and
applying energy from the electrical energy conducting element to the eye according to the total contact surface to cause shrinkage of corneal tissue of the eye,
wherein each of the plurality of outer segments is individually and separately moveable and each of the plurality of inner segments is individually and separately moveable.

18. The method of claim 17, wherein the total contact surface corresponds to the shape of a cornea.

19. The method of claim 17, wherein the plurality of outer segments and the plurality of inner segments are operable to adjust to the shape of the eye.

20. The method of claim 17, wherein the contact surface is positioned at the eye such that the contact surface applies a uniform pressure on the eye.

21. The method of claim 17, wherein the electrical energy conducting unit includes at least one biasing member, the at least one biasing member biasing the plurality of outer segments and the plurality of inner segments towards the distal end.

22. The method of claim 17, wherein the plurality of outer segments and the plurality of inner segments are substantially cylindrical at the distal end.

23. The method of claim 17 further comprising moving at least one outer segment to a position between the distal end and the proximal end.

24. The method of claim 23, wherein the position is selected such that the at least one outer segment does not contact the eye.

25. The method of claim 17 further comprising moving at least one inner segment to a position between the distal end and the proximal end.

26. The method of claim 25, wherein the position is selected such that the at least one inner segment does not contact the eye.

27. The method of claim 17 further comprising moving at least one outer segment and at least one inner segment to achieve at least one of the group consisting of a selected pattern of energy applied to the eye and a selected depth of penetration of energy into the eye.

28. The method of claim 27, wherein the pattern is asymmetric.

29. The method of claim 17 further comprising supplying energy from the electrical energy source to one or more outer segments and one or more inner segments.

30. The method of claim 29, wherein the energy is not supplied to at least one outer segment.

31. The method of claim 29, wherein the energy is not supplied to at least one inner segment.

32. The method of claim 17 further comprising selectively supplying energy to at least one outer segment and at least one inner segment to apply energy to a cornea according to an asymmetric pattern.

33. A system for applying thermokeratoplasty to an eye, the system comprising:
an electrical energy source; and
an electrical energy conducting element extending from a proximal end to a distal end, the energy conducting element electrically connected to the electrical energy source at the proximal end, the energy conducting element including:
an outer conductor extending along a longitudinal axis to the distal end, the longitudinal axis being generally in a direction from the proximal end to the distal end, the outer conductor having an interior surface, the outer conductor including a plurality of moveable outer segments, the plurality of moveable outer segments being configured to be individually and separately moveable along the longitudinal axis;
an inner conductor extending along the longitudinal axis to the distal end and disposed within the outer conductor, the inner conductor including a plurality of moveable inner segments, the plurality of moveable inner segments are configured to be individually and separately moveable along the longitudinal axis, the inner conductor having an exterior surface separated from the interior surface of the outer conductor by a gap, the gap extending entirely around the exterior surface of the inner conductor; and
a flexible sheath-like structure of dielectric material covering the distal end configured to substantially inhibit an electrical current from the inner conductor and the outer conductor into the corneal tissue, the plurality of outer segments and the plurality of inner segments forming a total contact surface at the distal end, the total contact surface being positionable at a corneal surface of an eye such that a microwave energy is applied to the eye according to the total contact surface to cause shrinkage of corneal tissue of the eye in response to the electrical connection between the energy conducting element and the electrical energy source.

\* \* \* \* \*